United States Patent [19]
Greer

[11] Patent Number: 5,925,324
[45] Date of Patent: Jul. 20, 1999

[54] MAGNETOHYDRODYNAMIC STERILIZATION METHOD AND APPARATUS

[75] Inventor: Joe Greer, Little Rock, Ark.

[73] Assignee: Paradigm Technologies, N. Little Rock, Ark.

[21] Appl. No.: 08/723,503

[22] Filed: Sep. 30, 1996

[51] Int. Cl.⁶ .................................. C02F 1/30; C02F 1/48
[52] U.S. Cl. .................. 422/186.03; 422/22; 422/186.01
[58] Field of Search ................................ 422/22, 186.01, 422/186.04, 186.03

[56] References Cited

U.S. PATENT DOCUMENTS

| 4,458,153 | 7/1984 | Wesley | 250/435 |
| 4,524,079 | 6/1985 | Hofmann | 426/234 |
| 4,601,823 | 7/1986 | Beck | 210/222 |
| 4,659,479 | 4/1987 | Stickler et al. | 210/695 |
| 4,879,045 | 11/1989 | Eggerichs | 210/695 |
| 5,326,530 | 7/1994 | Bridges | 422/22 |

*Primary Examiner*—Daniel J. Jenkins

[57] ABSTRACT

The MHD sterilization system invention is a method involving the use of magnetohydrodynamics, (MHD) for the specific purpose of destroying populations of microorganisms occurring in, within or on fluid, semi-fluid, semi-solid or solid materials.

11 Claims, 5 Drawing Sheets

SECTION X-X

MAGNETOHYDRODYNAMIC STERILIZATION METHOD AND APPARATUS

BACKGROUND

1. Field of Invention

This invention relates generally to sterilization processes for the elimination of microbes, specifically, the invention is directed to a sterilization method utilizing a magnetohydrodynamic, (MHD) cell and apparatus for destroying the microbes.

2. Description of Prior Art

The importance of sterilization processing is well known to both the general public and to those skilled in the art. Sterilization processes are required to obtain substantially 100% microbe elimination while not altering the material that is being sterilized. In addition, sterilization of waste streams is becoming of greater importance for environmental reasons. Typical materials that require sterilization are food products, pharmaceuticals, cosmetics and medical waste. Medical waste sterilization is becoming increasingly important with higher population densities and the new contagious diseases.

A wide variety of sterilization processes exist using a variety of temperature, electrical and/or chemical processes. All of these processes have certain draw backs. Sterilization processes that use an elevated temperature have the disadvantages of the energy requirements of heating the material to a temperature adequate to kill microbes and the effect that it has on the material being sterilized. Typical negative side-effects of thermal processes on foods are protein denaturation and degradation of vitamins.

Electrical sterilization has been tried and has even been patented. U.S. Pat. No. 1,863,222, issued Jun. 14, 1932 proposes a method of sterilization food with high frequency electrical oscillations. A vacuum tube oscillator is proposed for generating a high frequency electric field. Material to be treated is placed within a receptacle disposed across the electrodes. The recommended frequency of operation is between 60 and 600 MHz.

An electrical process called Electro-Pure Process was popular in the 1930's but the process fell out of favor by 1960. The reason for the discontinuance of the process could not be found. However many papers indicate that electrical sterilization has had the problem of an inadequate kill rate of microbes. In addition, the process has the disadvantage of not being sporocidal.

U.S. Pat. No. 4,524,079 issued Jun. 18, 1985, proposes a sterilization of food products having relatively high electric resistivity by subjecting them to the pulses of an oscillating magnetic field. Material to be sterilized is subjected to an intensity of approximately 2–100 Tesla at a frequency of about 5–500 KHz. The inventor claims to decrease the microorganism population by approximately two orders of magnitude through the application of a single pulse. This process also has the disadvantage of not being sporocidal.

BACKGROUND OF INVENTION

Recently the inventor, Sedley J. Greer, Jr. has been experimenting with a sterilization process through the phenomena of magnetohydrodynamics. As well recognized by those skilled in the art of physics, a MHD involves the simultaneous establishment of an electrical field transverse to a magnet field. Previous experiments have been conducted by the inventor of this case and patents were received for a Magnetohydrodynamic Geophone, U.S. Pat. No. 4,585,207 issued Apr. 15, 1985 and U.S. Pat. No. 4,764,908 issued Aug. 16, 1988.

Continuing experiments on MHD systems have revealed that the application of static or direct current fields to materials obtains sterilization effects beyond any of those achieved in the prior art. Stated another way, it was found that the combination of a sterilization pathway and a MHD transducer applying magnetic and electric fields transversely across the pathway, significantly sterilizes material. Microorganisms are rapidly killed and tests have revealed that sterilization is virtually 100% complete. Moreover, the application of oscillating fields is unnecessary. It is the unexpected synergy of both the magnetic and electrical fields on sterilization that make this invention unique.

It has been theorized that the physics of the invention are based primarily on ion velocities that are equal to or approach the same velocities of ions at boiling water temperatures. Using the typical conductivity of organic solutions, a one Tesla magnet and an electrical potential of 1000 volts, an University of Arkansas Professor of Physics estimated for the inventor that the $OH^-$ velocities were approximately equal to boiling water, ($10^3$ meters/second).

To summarize, one of the synergy's of using an MHD cell for sterilization is the material being sterilized is "boiled" without raising the temperature of the material. Other mechanisms of killing microbes could and likely do occur, but are not fully known a this time.

Actual experiments have been conducted and the results are plotted in FIG. 5. The figure shows the exponential decrease in microbe populations with higher magnetic flux levels, electrical power and application times. In actual test, spores were 100% eliminated by this process. Spore sterilization is considered to be the benchmark of any sterilization process.

OBJECTS AND ADVANTAGES

Accordingly, the objects and advantages of the present invention are:

(a) to provide a sterilization process that can be rapidly and economically applied to a wide variety of materials.

(b) to provide a sterilization process that does not involve the application of nuclear radiation, microwave energy, significant heat, or sterilizing chemicals to the material being treated.

(c) to provide a sterilization process that will not have harmful side-effects such as of vitamin and nutrient degradation to food.

(d) to provide a system of the character described capable of processing medical and veterinary waste.

(e) to provide a system that can economically sterilize waste water to aid in the reclamation and purification of water.

(f) to provide a system of the character described capable of processing meat, poultry and dairy food materials.

(g) to overcome the short comings of electricity or magnetism alone which liberates heat and/or electrolysis. MHD causes energy to be transformed into fluid flow without appreciable quantities of thermal energy.

Further objects and advantages of this invention will become apparent from a consideration of the drawings and ensuing description.

BRIEF DESCRIPTION OF THE DRAWINGS

In the following drawings, which form a part of the specification and which are to be construed in conjunction therewith, and in which like reference numerals have been employed throughout wherever possible to indicate like parts in the various views.

SUMMARY OF THE INVENTION

The MHD sterilization system invention is a method involving the specific use of magnetohydrodynamics, (MHD) for the specific purpose of destroying populations of micro-organisms occurring in, within or on fluid, semi-fluid, semi-solid or solid materials.

The MHD sterilization method uses magnetohydrodynamic effects to sterilize materials conducted through a passageway or a static cell. The MHD cell consists of a fluid containment passageway with electrodes positioned between the poles of a magnet. A current is sent transversely through the fluid at a right angle to the magnetic field. The system is completely sealed and has no moving parts other than the fluid itself. The crossed electric and magnet fields induce ion motions that meets or exceeds the ion velocities that exist in boiling water. It is theorized that these velocities along with other phenomena kill any existing microbes that may exist in the fluid.

In the "through a passageway" or flow through MHD sterilization system, the material flows past a velocity transducer to measure flow and a conductivity transducer to measure the material's conductivity. A flow control valve is located in the material conduit and is controlled by the system computer. The valve's purpose is to keep the flow from exceeding the system's ability to sterilize effectively.

The system computer compares the flow and conductivity measurements and instructs the controlled power supply to provide the correct potential across the MHD cell electrodes.

Material exiting the flow through MHD cell should be thoroughly sterilized and ready for human or animal consumption or safe environmental disposal.

In the static cell MHD sterilization system, the material is placed in a perforated plastic strainer and lowered into a closed ended MHD cell charged with a mildly saline solution. Room is left toward the top of the cell to allow for the fluid surge that occurs with MHD cell activity.

A conductivity measurement is taken using a conductivity transducer. The system computer evaluates the conductivity measurements and instructs the controlled power supply to provide the correct potential across the MHD cell electrodes for a time adequate to insure sterilization. The computer would indicate to the operator when the sterilization process is complete by audio and/or visual means. The operator could then lift the perforated plastic strainer and remove the material being sterilized.

DESCRIPTION OF INVENTION

Figure 1:
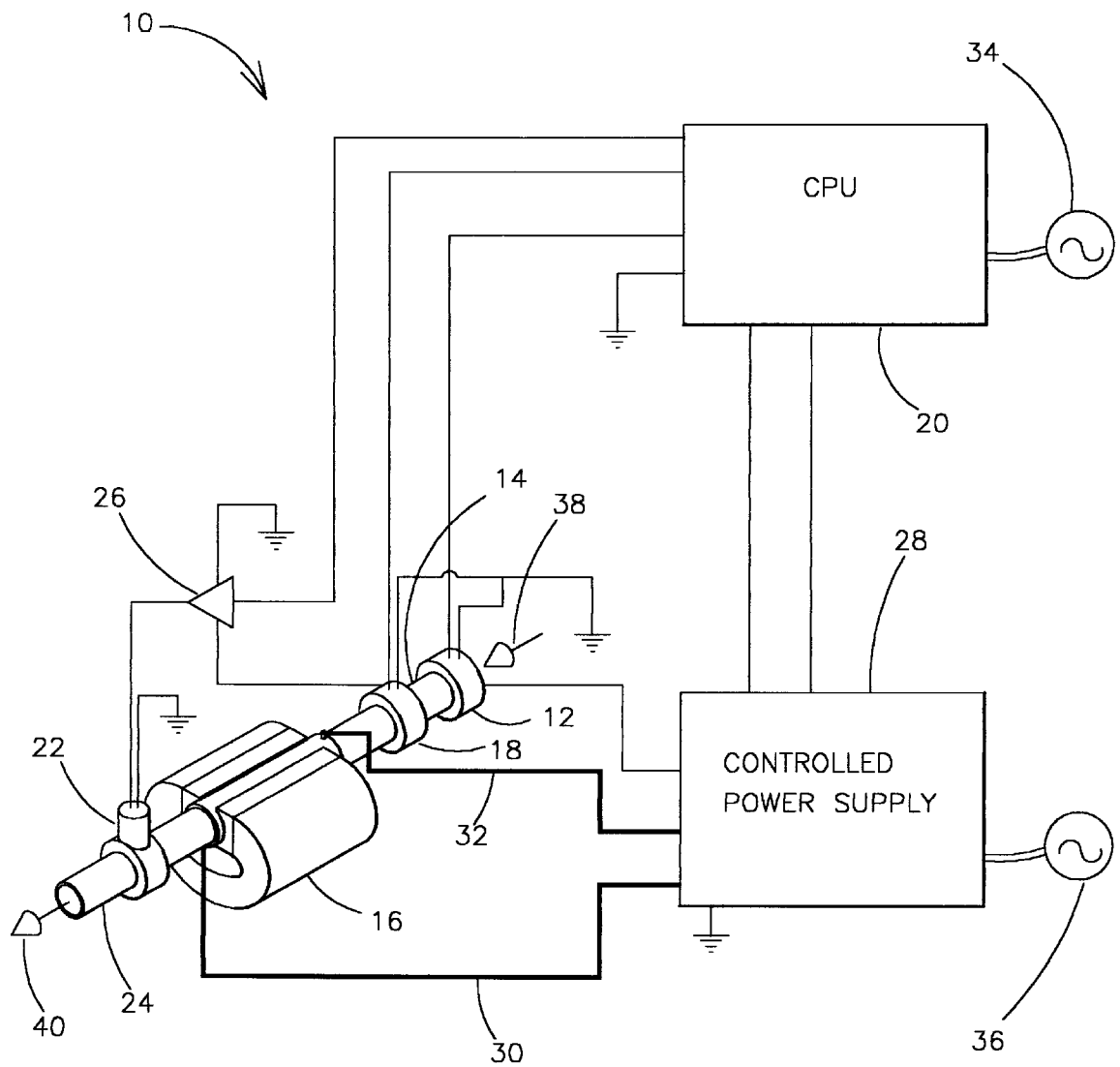
FIG. 1 is a fragmentary, diagrammatic and pictorial view showing the preferred Magnetohydrodynamic Sterilization Flow Through Type System.

With initial reference directed to FIG. 1, the best mode of the present invention for a flow-through MHD sterilization system has been generally designated by the reference numeral 10. At the outset, it should be understood that the configuration herein disclosed may take on a variety of forms, although we have presently disclosed what we now believe to be the best mode.

Ideally the system would consist of a flow transducer 12 which is in an inlet conduit line 14 leading to a MHD flow through cell 16. A material flow to be sterilized is represented by arrows 38 and 40. Mounted in between the flow transducer 12 and the MHD flow through cell 16 is a conductivity transducer 18. Both the conductivity transducer 18 and the flow transducer 12 are non-restrictive to the material flow running through inlet conduit line 14. The output signals from the flow transducer 12 and the conductivity transducer 18 are electrically connected to a Central Processing Unit, CPU 20. CPU 20 is electrically connected to line voltage 34. An electrically operated flow control valve 22 is mounted in an output conduit 24 and regulates the amount of material flow going through the MHD flow through cell 16. The flow control valve 22 is electrically connected to a valve controller 26. The valve controller 26 receives a signal from CPU 20 based upon the output signals from the flow transducer 12 and conductivity transducer 18. A controlled power supply 28 provides power to valve controller 26 and the MHD flow through cell 16. The controlled power supply 28 receives its electrical power from line voltage 34. An electrical cable 30 and an electrical cable 32 transmits direct current electrical power from the controlled power supply 28 to the MHD flow through cell 16. The valve controller 26 sends electrical power to the flow control valve 22 to open or close the valve enough so that the fluid flow going through the MHD flow through cell 16 is at the correct level. The valve controller 26 is controlled by an electrical signal that is received from the CPU 20.

The flow control valve 22 will remain fully open unless insufficient material conductivity exists as measured by conductivity transducer 18 in relation to the material flow as measured by the flow transducer 12.

Under ideal operating conditions, sufficient material conductivity would exist and the CPU 20 would send an electrical signal to controlled power supply 28 which would then regulate the voltage potential between electrical cables 30 and 32. The voltage potential would correspond to the necessary voltage required for a full microbe kill at the known magnet strength of the MHD flow through cell 16, the fluid conductivity and the fluid flow rate.

If insufficient conductivity exists with respect to the flow rate, The CPU 20 would send an electrical signal to controlled power supply 28 to maximize the voltage potential between electrical cables 30 and 32. The CPU 20 would also send an electrical signal to valve controller 26 which would throttle the flow control valve 22 to reduce the material flow rate to a level that the maximum voltage potential between electrical cables 30 and 32 will enact a full microbe kill.

Because the sterilization is being performed by an MHD cell, it is possible that sufficient pressure rise across the MHD flow through cell 16 would be a sufficient pump for the sterilization system to work. This is because the application of sufficient transverse electrical and magnetic fields across the pathway, normal to the direction of displacement, will generate fluid motion through magnetohydrodynamic effects.

Figure 2A:
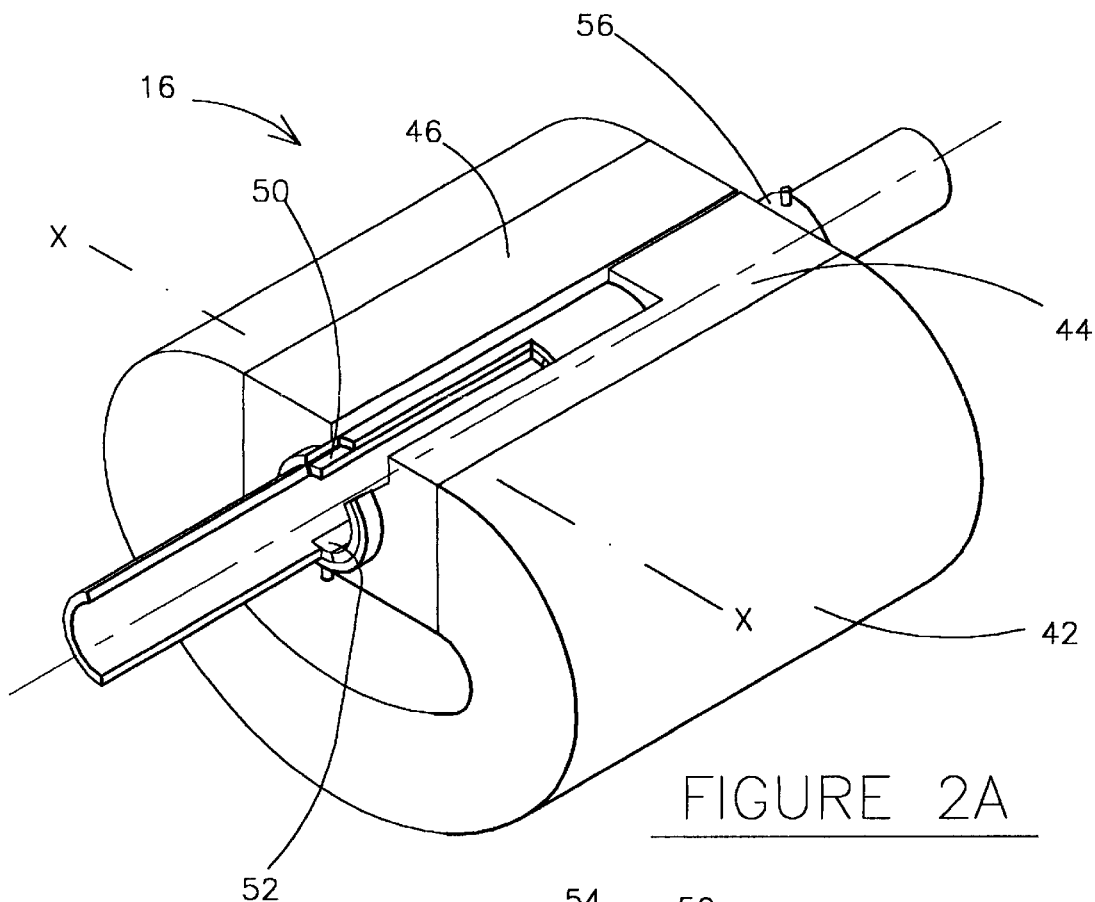
FIG. 2A is an enlarged fragmentary, isometric view of the preferred Magnetohydrodynamic Flow Through Type Cell.
Figure 2B:
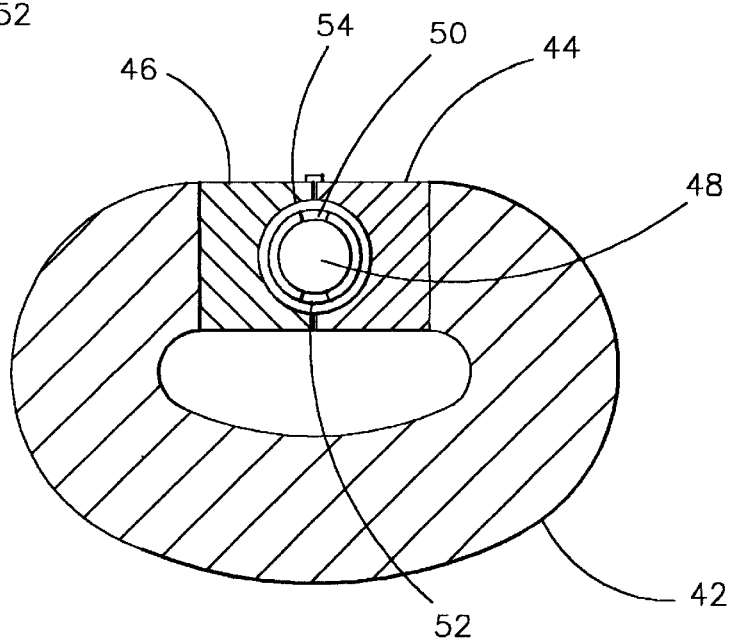
FIG. 2B is an enlarged sectional view of the preferred Magnetohydrodynamic Flow Through Type Cell.

With concurrent reference now directed to FIGS. 2A and 2B, the MHD flow through cell 16 comprises a rigid, generally C-shaped, high performance permanent or electromagnet 42 which transmits a magnetic field across its poles 44 and 46, which extends generally perpendicularly to the direction of material flow through a passageway 48.

MHD electrodes 50 and 52 are disposed on the top and the bottom of passageway 48 as depicted and are permanently secured within suitable slots defined at the top and bottom of the passageway 48. These electrodes are maintained in place within the magnet between poles 44 and 46 by a tubular sheath 54 that encloses the electrodes 50 and 52 and that portion of the passageway 48 confined between magnet poles 44 and 46. An electrical potential and thus an electrical field is applied across these electrodes. This electric field is oriented perpendicularly to the magnetic field established between the poles 44 and 46. Further, the magnetic field and the electric field are both perpendicular to the direction of material flow through passageway 48. Microbe killing is accomplished by the crossed electric and magnetic fields inducing high, (approximately $10^3$ meters/sec), ion velocities. With this construction, the magnetic field applied between poles 44 and 46 is preferably in the 1 to 5 Tesla range. The voltage required for high performance sterilization is between 100 and 1000 volts.

Figure 3:
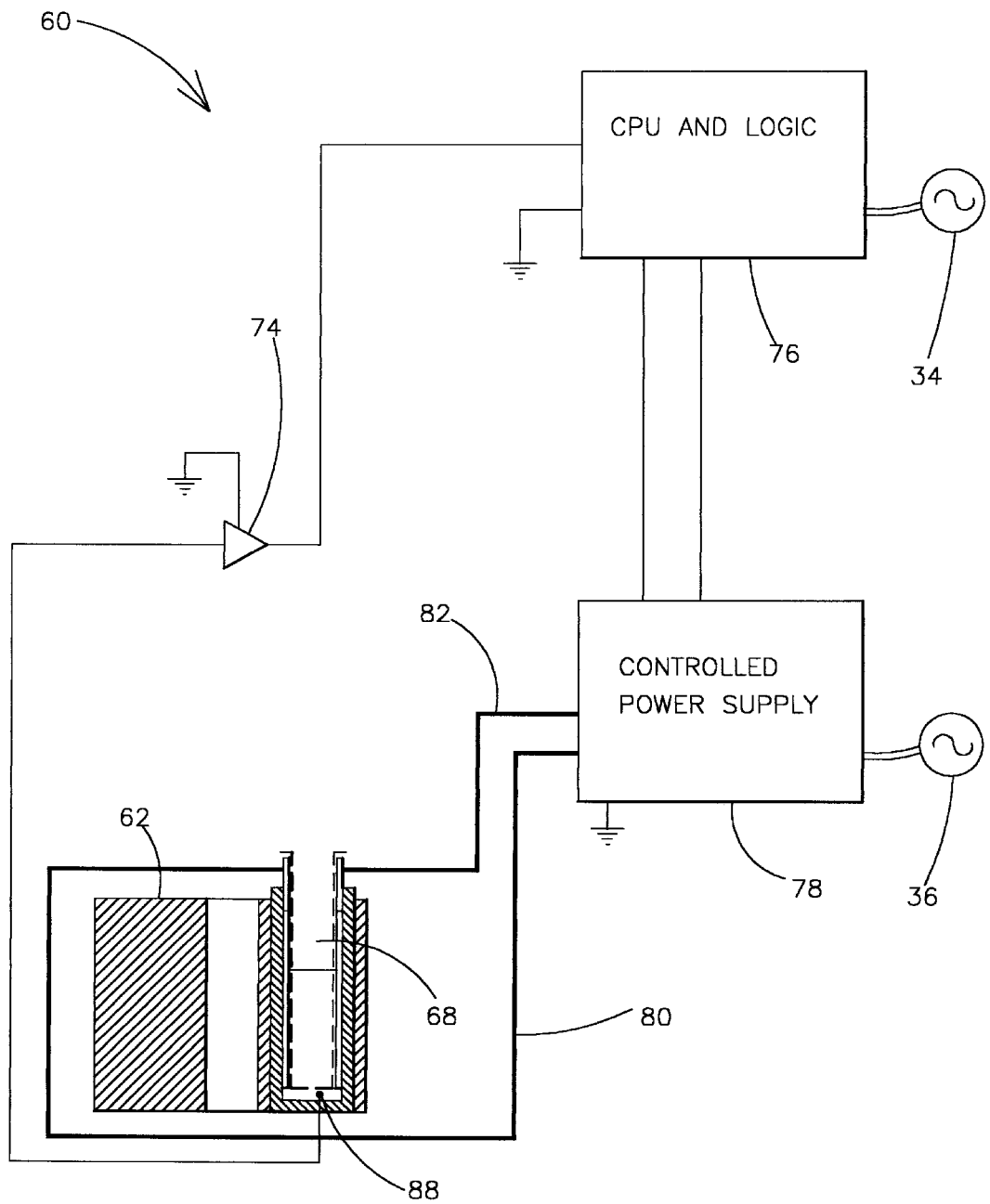
FIG. 3 is a fragmentary, diagrammatic and sectional view of the preferred Magnetohydrodynamic Static Type Cell.
Figure 4:
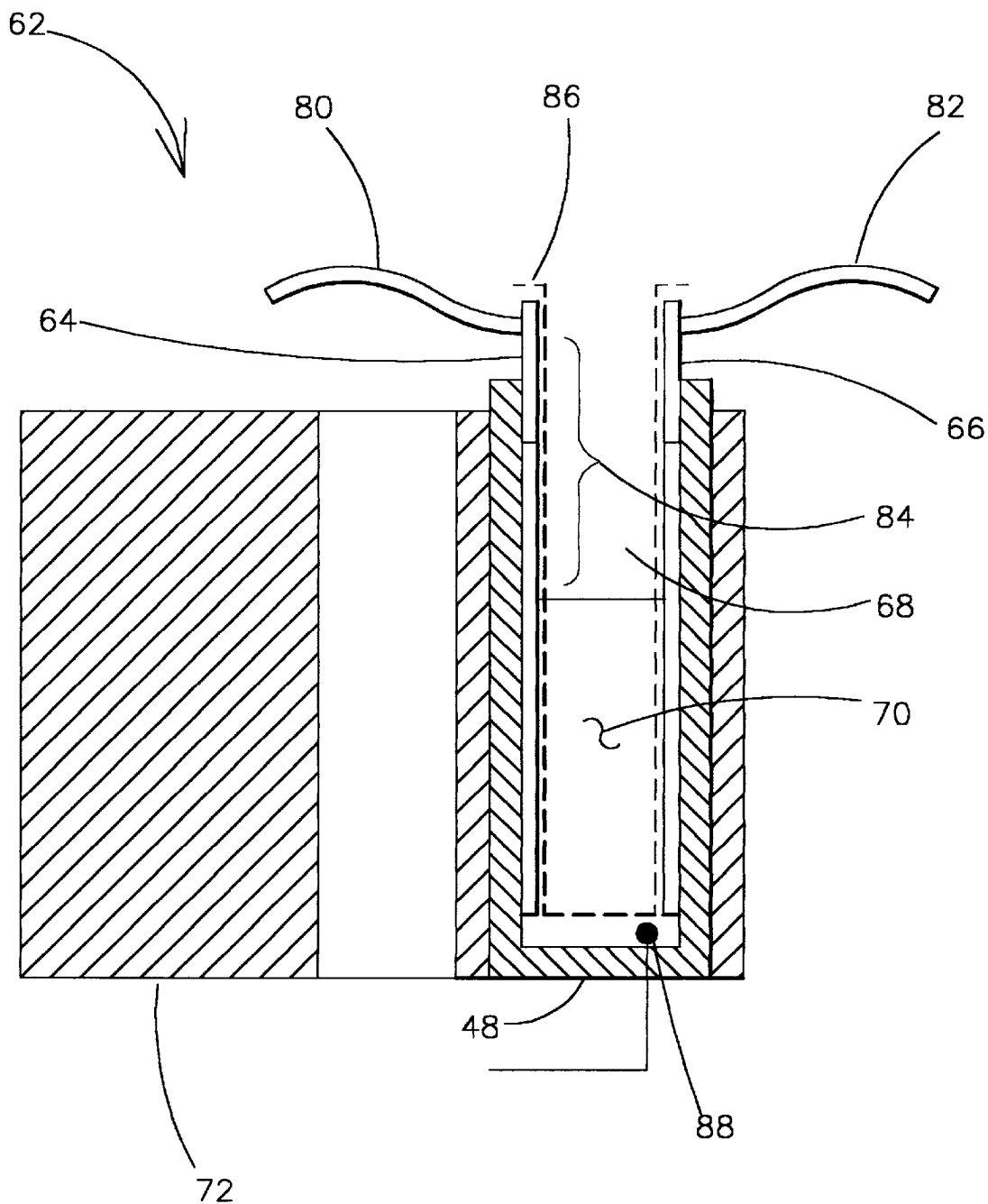
FIG. 4 is an enlarged sectional view of the preferred Magnetohydrodynamic Static Type Cell.
Figure 5:
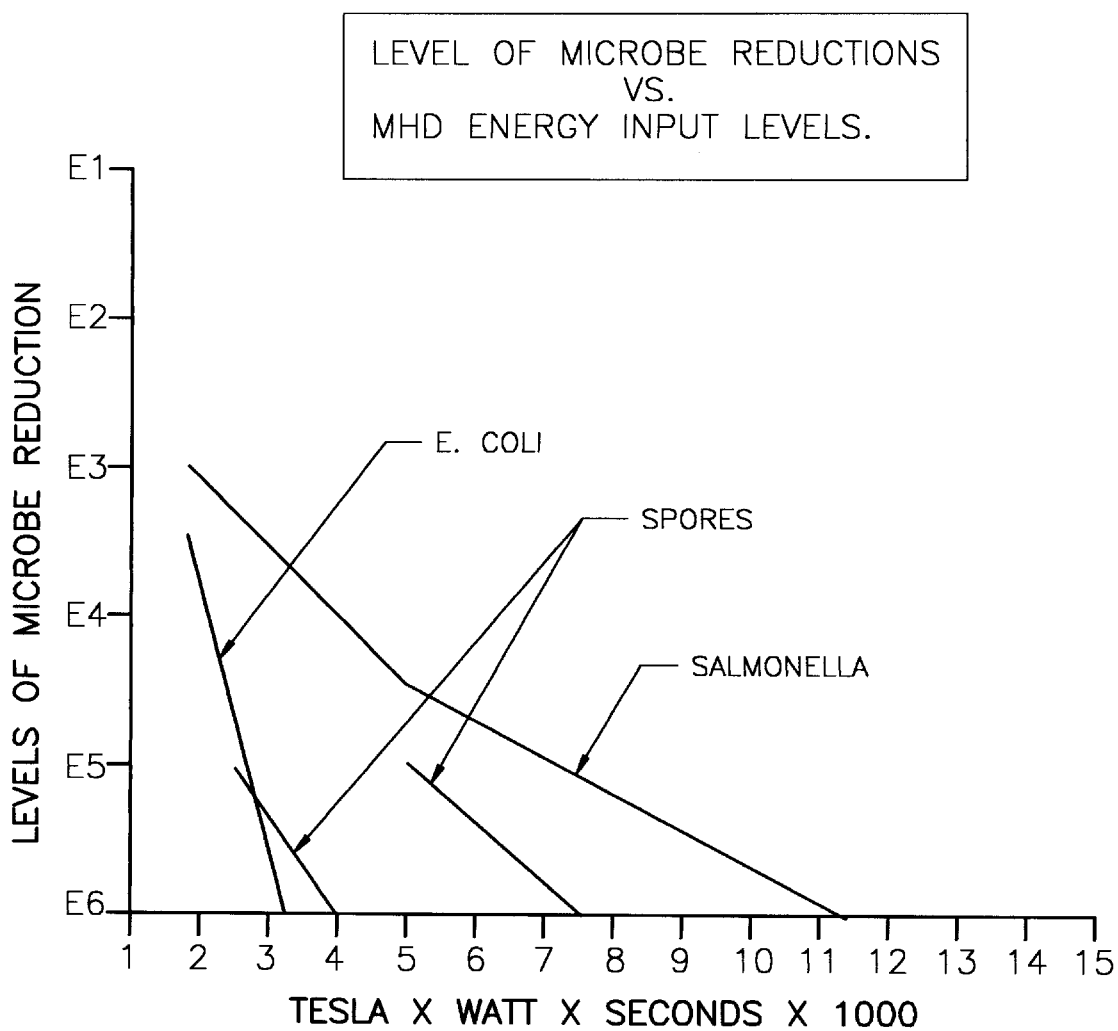
FIG. 5 is a graph dictating the actual results of experiments using the concept of the present invention.

With reference now directed to FIGS. 3 and 4, the best mode of the present invention for a static cell MHD sterilization system has been generally designated by the reference numeral 60.

Ideally the system would consist of a static MHD cell 62. This static MHD cell 62 is similar in construction to the flow through MHD cell 16 except stood on end and the passageway closed off. The static MHD cell has an electrode 64 and 66 on opposite sides of an single open-ended passageway 68. A large C shaped permanent or electromagnet 72 is provided to create a magnetic field perpendicular to the electric field established between electrodes 64 and 65. A working fluid 70 partially fills the passageway 68. The working fluid 70 is a mildly saline solution unless the static cell is used for small batch fluid sterilization. Typically the matter being sterilized, such as medical instruments, is placed in the working fluid 70. A perforated plastic strainer 86 is provided to keep metallic components from contacting the electrodes and to allow easy removal of any solid material being sterilized.

A solid state signal conditioner 74 is electrically connected to a conductivity transducer 88 for measuring the conductivity of the working fluid 70. The output of conditioner 74 is electrically connected to a Central Processing Unit, CPU 76. CPU 76 would typically be electrically connected to line voltage 34. A controlled power supply 78 is provided to provide direct current electric potential to the static MHD cell 62 electrodes 64 and 66. The controlled power supply 78 receives its electrical power from line voltage 36. An electrical cable 80 and an electrical cable 82 transmits electrical power from the controlled power supply 80 to the static MHD cell 62 electrodes 64 and 66.

Under operating conditions, the CPU 76 would monitor the fluid conductivity by the signal received from signal conditioner 74. The CPU 76 would then send an electrical signal to controlled power supply 78 which would in turn regulate the voltage potential between electrical cables 80 and 82. The CPU 76 would create an audio and/or visual alarm to let the operator know that the sterilization process is complete. The voltage potential and application time would correspond to the necessary values required for a full microbe kill at the known magnet strength of the static MHD cell 62 and the working fluid 70 conductivity. Microbe killing is accomplished by the crossed electric and magnetic fields inducing high, (approximately $10^3$ meters/sec), ion velocities. With this construction, the magnetic field is preferably in the 1 to 5 Tesla range. The voltage required for high performance sterilization is between 100 and 1000 volts.

Because the sterilization is being performed by an MHD cell a surge zone 84 is allowed at the top of the static MHD cell 62. This is necessary because the application of sufficient transverse electrical and magnetic fields across the pathway, normal to the direction of displacement, will generate fluid motion through magnetohydrodynamic effects.

It should be understood that the control circuits described in FIGS. 1 and 3 are the best known mode at this time. However, because of the continuing experiments, it is contemplated that changes in the circuitry may occur. As can be recognized by those with skill in the electronic arts, a variety of different approaches could be used to provide similar results.

From the foregoing, it will be seen that this invention is one well adapted to obtain all the ends and objects herein set forth, together with other advantages that are inherent to the structure.

While the above description contains many specifications, these should not be construed as limitations on the scope of the invention, but rather as an exemplification of one preferred embodiment thereof Many other variations are possible. For example an alternating or pulsed current could be used across the MHD electrodes to induce the necessary ion velocity in the fluid with only the fluid motive force being lost but still the sterilization effect in place. Many control circuits could be created that could deliver electric power to an MHD cell used for sterilization.

Accordingly, the scope of the invention should be determined not by the embodiments illustrated, but by the appended claims and their legal equivalents.

I claim:

1. A method of sterilizing material by flowing said material through a magnetohydrodynamic cell, said magnetohydrodynamic cell comprising:

a passageway for said material being sterilized to pass; and, means for establishing an adequate magnetic field that is substantially perpendicular to said passageway; and, means for concurrently generating an adequate electrical field substantially normal to said magnetic field and said passageway wherein said means for establishing the magnetic field comprises a means to substantially enclose the cell.

2. The method of sterilizing material as defined in claim 1 wherein said means for establishing an adequate magnetic field is a permanent magnet.

3. The method of sterilizing material as defined in claim 1 wherein said means for establishing an adequate magnetic field is an electromagnet.

4. The method of sterilizing material as defined in claim 1 wherein said means for generating an adequate electrical field comprises:

a set of two electrodes running axially along and opposed to each other along said passageway, said set of two electrodes extending substantially the entire length of said adequate magnetic field, said set of two electrodes being located along the radially outer wall of said passageway; said set of two electrodes having an electrical potential relative to each other, said electrical potential being generated by a power supply means.

5. The method of sterilizing material as defined in claim 1 further comprising:

means for monitoring the conductivity of said material, and, means to regulate the said adequate electrical field in response to said means for monitoring the materials conductivity whereby to insure sterilization of said material.

6. The method of sterilizing material as defined in claim 1 further comprising:

means for monitoring the conductivity of said material, and, means for monitoring the flow rate of said material, and, means to regulate the flow rate of said material, and, means to regulate the said adequate electrical field in response to said means for monitoring the materials conductivity and said means for monitoring the material flow rate whereby to insure sterilization of said material and to not exceed the maximum effective sterilization flow rate of the said magnetohydrodynamic cell.

7. An apparatus for sterilizing material comprising:

a magnetohydrodynamic sterilization cell, said magnetohydrodynamic sterilization cell comprising:

a passageway for material to be sterilized, said passageway being closed on one end; and, means for establishing a magnetic field that is substantially perpendicular to said passageway; and, means for concurrently generating an electrical field substantially normal to said magnetic field and said passageway wherein said means for establishing the magnetic field comprises a means to substantially enclose the cell.

8. The apparatus for sterilizing material as defined in claim 7 wherein said means for establishing a magnetic field is a permanent magnet.

9. The apparatus for sterilizing material as defined in claim 7 wherein said means for establishing a magnetic field is an electromagnet.

10. The apparatus for sterilizing material as defined in claim 7 wherein said means for generating an electrical field comprises:

a set of two electrodes running axially along and opposed to each other along said passageway, said set of two electrodes extending substantially the entire length of said magnetic field, said set of two electrodes being located along the radially outer wall of said passageway; said set of two electrodes having an electrical potential relative to each other, said electrical potential being generated by a power supply means.

11. The apparatus for sterilizing material as defined in claim 7 further comprising:

means for monitoring the conductivity of said material, and, means to regulate the said electrical field in response to said means for monitoring the materials conductivity whereby to insure sterilization of said material.

* * * * *